United States Patent
Mak et al.

(10) Patent No.: US 10,705,323 B2
(45) Date of Patent: Jul. 7, 2020

(54) SURGICAL MICROSCOPE SYSTEM WITH AUTOMATIC ZOOM CONTROL

(71) Applicants: Siu Wai Jacky Mak, Toronto (CA); Tammy Lee, Toronto (CA)

(72) Inventors: Siu Wai Jacky Mak, Toronto (CA); Tammy Lee, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 11 days.

(21) Appl. No.: 15/961,318

(22) Filed: Apr. 24, 2018

(65) Prior Publication Data

US 2019/0324252 A1  Oct. 24, 2019

(51) Int. Cl.
| | |
|---|---|
| *G02B 21/02* | (2006.01) |
| *G02B 21/00* | (2006.01) |
| *H04N 5/232* | (2006.01) |
| *G02B 21/36* | (2006.01) |
| *G02B 21/06* | (2006.01) |

(52) U.S. Cl.
CPC ....... *G02B 21/025* (2013.01); *G02B 21/0012* (2013.01); *G02B 21/06* (2013.01); *G02B 21/365* (2013.01); *H04N 5/23216* (2013.01); *H04N 5/23296* (2013.01)

(58) Field of Classification Search
CPC .............. G02B 21/025; G02B 21/0012; H04N 5/23216
USPC .......................................................... 348/79
See application file for complete search history.

(56) References Cited

U.S. PATENT DOCUMENTS

| | | | | |
|---|---|---|---|---|
| 5,805,335 A | * | 9/1998 | Fukaya .................. | G02B 7/001 359/384 |
| 6,005,710 A | * | 12/1999 | Pensel .................. | A61B 3/0025 359/379 |
| 2005/0041282 A1 | * | 2/2005 | Rudolph ................ | G02B 7/001 359/368 |
| 2010/0302629 A1 | * | 12/2010 | Steffen ............... | G02B 21/0012 359/385 |
| 2010/0312095 A1 | * | 12/2010 | Jenkins .................. | A61B 5/415 600/411 |
| 2017/0082847 A1 | | 3/2017 | Wilzbach et al. | |

FOREIGN PATENT DOCUMENTS

| | | |
|---|---|---|
| EP | 3536217 | 9/2019 |
| GB | 2571857 | 9/2019 |
| WO | 2016/154589 | 9/2016 |

OTHER PUBLICATIONS

Search Report issued by the Intellectual Property Office of the United Kingdom in relation to corresponding GB Application No. GB1905746.2 dated Oct. 21, 2019, 3 pgs.

* cited by examiner

*Primary Examiner* — Joseph G Ustaris
*Assistant Examiner* — Amir Shahnami
(74) *Attorney, Agent, or Firm* — Ridout & Maybee LLP

(57) ABSTRACT

A surgical microscope system for use in a medical procedure. The surgical microscope system is controlled in a first mode of operation corresponding to a phase of the medical procedure and defining at least one setting for adjusting a set of adjustable optics. While in the first mode of operation, the surgical microscope system automatically determines, from a captured image, an indication that a second mode of operation is relevant. The mode of operation is switched to the second mode of operation.

19 Claims, 9 Drawing Sheets

SURGICAL MICROSCOPE SYSTEM WITH AUTOMATIC ZOOM CONTROL

FIELD

The present disclosure is generally related to surgical microscopes, including motorized surgical microscopes suitable for use in image guided medical procedures.

BACKGROUND

A surgical microscope is an important tool in many medical procedures, including procedures performed on the spine and brain. With current advances in optics and digital microscopes, surgeons are able to operate with more visualization power, including higher resolution and higher magnification, allowing surgeons to see much finer details in the surgical field. Surgeons are becoming increasingly accustomed to zooming in to see the details of the anatomy and operating at higher magnifications. It is common for surgeons to switch and select different zoom settings for different steps of a procedure.

There is a tradeoff in any surgical microscope—the higher the magnification and optical resolution that the surgeon utilizes, the smaller the depth of field of the captured image. In procedures, such as spine and brain surgeries, where the surgical field can be quite deep (e.g., in minimal invasive surgeries), this means that the entire surgical field cannot stay in focus at high magnification. When the entire field of interest cannot be in focus, a surgeon may switch to a lower magnification to gain a larger depth of field to focus the entire field of interest. This may be frustrating and time-consuming for the surgeon, if the surgeon repeatedly changes magnification. Alternatively, the surgeon may keep a higher magnification, but repeatedly switch the focus region (e.g., manually or with tracked tools such as tracked pointers or suction tools) to keep the operating region in focus. Manually changing the focus region may be frustrating and time-consuming. Using a tracked tool to change the focus region may require the surgeon to switch between a currently used tool and the tracked tool, which can also be frustrating and time-consuming for the surgeon. Another approach using tracked tools is for all tools used in the procedure to be trackable. This can be expensive and computationally burdensome for the tracking system. Further, adding trackable markers to all tools can sacrifices usability and comfort level of the tools.

It would be useful to provide a solution that can change the magnification and/or focus of the captured image, with consideration of one or more of the above concerns.

SUMMARY

In some aspects of the present disclosure, there is described a surgical microscope system for use in a medical procedure. The surgical microscope system includes an optical assembly including a set of adjustable optics; one or more cameras coupled to the optical assembly for capturing at least one image of a field of view; and a controller coupled to the optical assembly for controlling the optical assembly to adjust the set of adjustable optics, the controller being coupled to the one or more cameras for receiving the captured image. The controller is configured to: set a first mode of operation to be a selected mode of operation, the first mode of operation corresponding to at least one phase of the medical procedure and defining at least one setting for adjusting the set of adjustable optics. The controller is also configured to: while controlling the optical assembly to adjust the optics according to the at least one setting defined by the selected mode of operation: determine, from the captured image, an indication that a second mode of operation is relevant, the second mode of operation defining at least one other setting for adjusting the set of adjustable optics; and change the selected mode of operation to be the second mode of operation. The controller is also configured to: control the optical assembly to adjust the optics according to the at least one other setting defined by the second mode of operation.

In some aspects of the present disclosure, there is described a method for controlling a surgical microscope system during a medical procedure. The method includes: setting a first mode of operation to be a selected mode of operation, the first mode of operation corresponding to at least one phase of the medical procedure and defining at least one setting for adjusting a set of adjustable optics of the surgical microscope system, to enable the surgical microscope system to capture at least one image of a field of view. The method also includes: while controlling the surgical microscope system according to the at least one setting defined by the selected mode of operation: determining, from the captured image, an indication that a second mode of operation is relevant, the second mode of operation defining at least one other setting for adjusting the set of adjustable optics; and changing the selected mode of operation to be the second mode of operation. The method also includes: controlling the surgical microscope system to adjust the optics according to the at least one other setting defined by the second mode of operation.

In some aspects of the present disclosure, there is described a system for performing a medical procedure. The system includes a surgical microscope including: an optical assembly including a set of adjustable optics; and one or more cameras coupled to the optical assembly for capturing at least one image of a field of view. The system also includes: a display for displaying the captured image; and a controller in communication with the surgical microscope. The controller is configured to: set a first mode of operation of the surgical microscope to be a selected mode of operation, the first mode of operation corresponding to at least one phase of the medical procedure and defining at least one setting for adjusting the set of adjustable optics. The controller is also configured to: while controlling the optical assembly to adjust the optics according to the at least one setting defined by the selected mode of operation: determine, from the captured image, an indication that a second mode of operation is relevant, the second mode of operation defining at least one other setting for adjusting the set of adjustable optics; and change the selected mode of operation to be the second mode of operation. The controller is also configured to: control the optical assembly to adjust the optics according to the at least one other setting defined by the second mode of operation.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
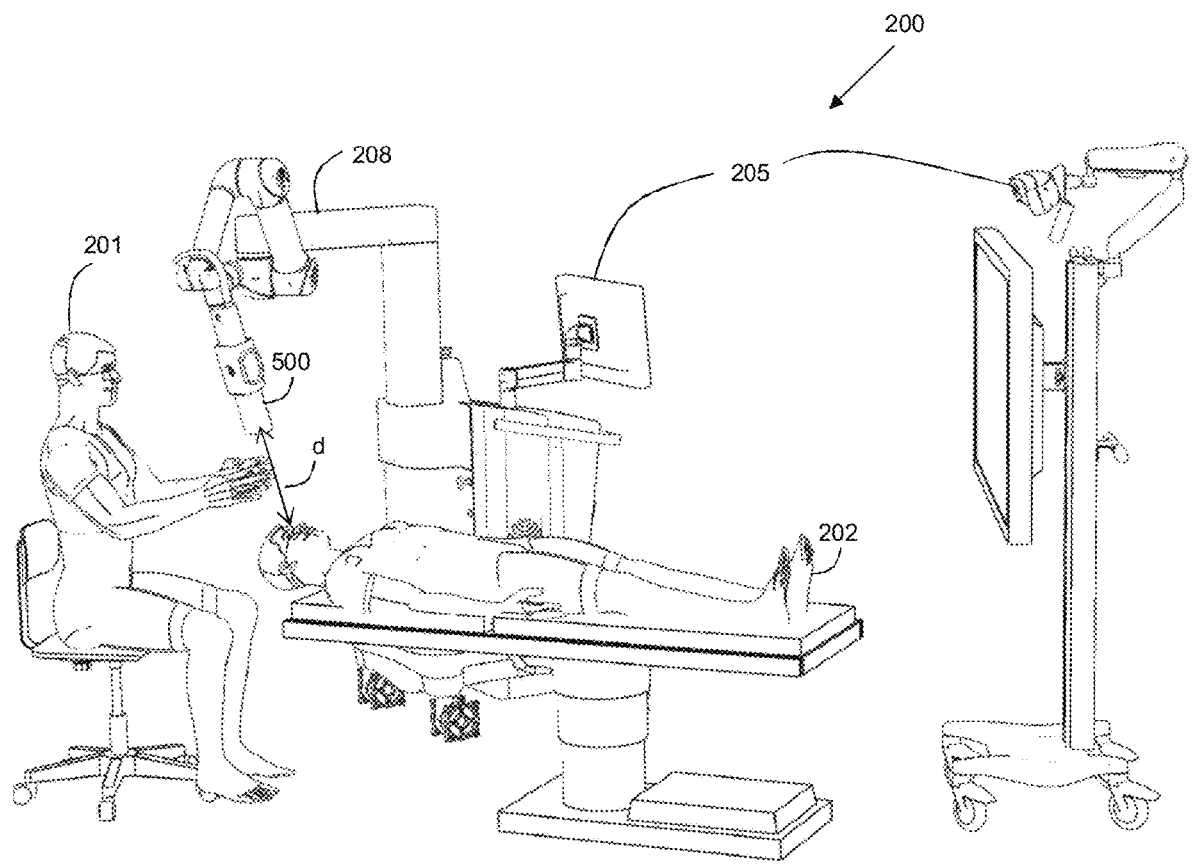
FIG. 1 shows an example surgical microscope system used in an image guided medical procedure.

The systems and methods described herein may be useful in image guided medical procedures, such as procedures in the field of spinal surgery or in the field of neurosurgery (e.g., including oncological care, neurodegenerative disease, stroke, brain trauma and orthopedic surgery). The teachings of the present disclosure may be applicable to other conditions or fields of medicine. It should be noted that while the present disclosure describes examples in the context of neurosurgery, the present disclosure may be applicable to other surgical procedures that may use intraoperative optical imaging.

Various example apparatuses or processes will be described below. No example embodiment described below limits any claimed embodiment and any claimed embodiments may cover processes or apparatuses that differ from those examples described below. The claimed embodiments are not limited to apparatuses or processes having all of the features of any one apparatus or process described below or to features common to multiple or all of the apparatuses or processes described below. It is possible that an apparatus or process described below is not part of any claimed embodiment.

Furthermore, numerous specific details are set forth in order to provide a thorough understanding of the disclosure. However, it will be understood by those of ordinary skill in the art that the embodiments described herein may be practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" may be understood to mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port. The present disclosure applies equally well to other medical procedures performed on other parts of the body, as well as to medical procedures that do not use an access port. Various examples of the present disclosure may be generally suitable for use in any medical procedure that may use surgical microscopes, for example any medical procedure that may benefit from having intraoperative imaging at different magnification and/or focus settings.

In FIG. 1, an exemplary navigation system environment 200 is shown, which may be used to support an image guided medical procedure. As shown in FIG. 1, a surgeon 201 conducts a surgery on a patient 202 in an operating room (OR) environment. A medical navigation system 205 may include an equipment tower, tracking system, display(s) and tracked instrument(s) (described further below) to assist the surgeon 201 during the procedure. A surgical microscope system 500 may be supported at a distal end of a robotic arm of a positioning system 208. The surgical microscope system 500 may be used to capture images (e.g., a static image or frames of a video) of the surgical site, and the captured images may be displayed on one or more displays for viewing by the surgeon 201.

Although FIG. 1 shows the surgical microscope system 500 being used in the context of a navigation system environment 200 (e.g., being controlled as part of the navigation system 205), the surgical microscope system 500 may also be used outside of a navigation system environment (e.g., without any navigation support).

The position and orientation of the surgical microscope system 500 may be determined based on tracking by the navigation system 205 (if used) and/or based on the position and orientation of the positioning system 208 (if the surgical microscope system 500 is supported by the positioning system 208). The distance d between the surgical microscope system 500 (more specifically, the aperture of the surgical microscope system 500) and the viewing target (e.g., the surface of the surgical site) may be referred to as the working distance. The surgical microscope system 500 may be designed to be used in a predefined range of working distance (e.g., in the range of about 15 cm to about 75 cm). It should be noted that, if the surgical microscope system 500 is mounted on the positioning system 208, the actual available range of working distance may be dependent on both the working distance of the surgical microscope system 500 as well as the workspace and kinematics of the positioning system 208.

Figure 2:
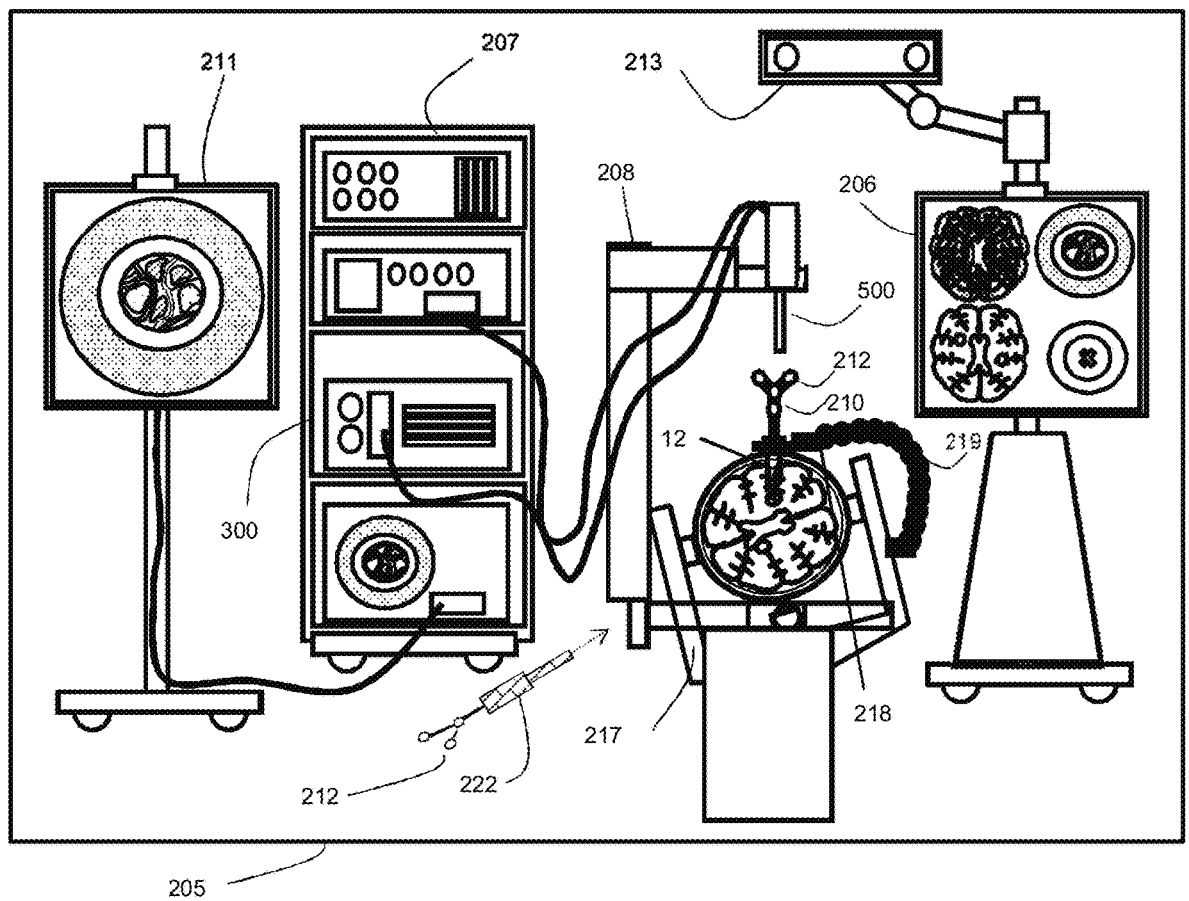
FIG. 2 is a diagram illustrating system components of an example navigation system, which may include an example surgical microscope system.

FIG. 2 shows a diagram illustrating an example navigation system 205 in greater detail. The disclosed surgical microscope system 500 may be used in the context of the navigation system 205, and in some embodiments may be part of the navigation system 205. The navigation system 205 may include one or more displays 206, 211 for displaying a static or video image, an equipment tower 207, and the positioning system 208, which may support the surgical microscope system 500 (described further below). The positioning system 208 may include a robotic arm. The robotic arm may have multiple joints, for example to enable up to five or six degrees-of-freedom. The robotic arm may support different tools at the distal end, such as the surgical microscope system 500. Other end effectors may be attached to the distal end of the robotic arm. In some examples, multiple end effectors may be attached to the distal end of the robotic arm, and the positioning system 208 may control the robotic arm to switch among different end effectors.

One or more of the displays 206, 211 may include a touch-sensitive display for receiving touch input. One or more of the displays 206, 211 may provide a 3D display (e.g., with or without the need to use 3D viewing goggles). The equipment tower 207 may be mounted on a frame (e.g., a rack or cart) and may contain a power supply and a control and processing unit 300 (described further below) that may execute planning software, navigation software and/or other software to manage the displays 206, 211, the positioning system 208, the surgical microscope system 500 and/or one or more medical instruments, for example. In some examples, the equipment tower 207 may be a single tower configuration operating with dual displays 206, 211, however other configurations may also exist (e.g., dual tower, single display, etc.). Furthermore, the equipment tower 207 may also be configured with a universal power supply (UPS) to provide for emergency power, in addition to a regular AC adapter power supply.

A portion of the patient's anatomy may be held in place by a holder. For example, for a neurosurgery procedure, the patient's head and brain may be held in place by a head holder 217. An access port 12 and associated introducer 210 may be inserted into the head, to provide access to a surgical site in the head. The surgical microscope system 500 may be used to view down the access port 12 at a sufficient magnification to allow for enhanced visibility down the access port 12. The surgical microscope system 500 may communicate with the control and processing unit 300, for example to receive instructions from the control and processing unit 300 and/or to display captured images on the displays 206, 211.

In some examples, the navigation system 205 may include a tracked pointer 222. The tracked pointer 222, which may include trackable markers 212 to enable tracking by a tracking camera 213, may be used to identify points (e.g., fiducial points) on a patient. An operator, typically a nurse or the surgeon 201, may use the tracked pointer 222 to identify the location of points on the patient 202, in order to register the location of selected points on the patient 202 in the navigation system 205. In some examples, the positioning system 208 may be used to move the tracked pointer 222.

Tracking markers 212 may be connected to the introducer 210 for tracking by the tracking camera 213, which may provide positional information of the introducer 210. In some examples, the tracking markers 212 may be alternatively or additionally attached to the access port 12. In some examples, the tracking camera 213 may be a 3D infrared optical tracking stereo camera similar to one made by Northern Digital Imaging (NDI). In some examples, the tracking camera 213 may be instead an electromagnetic system (not shown), such as a field transmitter that may use one or more receiver coils as tracking markers 212. A known profile of the electromagnetic field and known position of receiver coil(s) relative to each other may be used to infer the location of the tracked tool using the induced signals and their phases in each of the receiver coils. Operation and examples of this technology is further explained in Chapter 2 of "Image-Guided Interventions Technology and Application," Peters, T.; Cleary, K., 2008, ISBN: 978-0-387-72856-7, incorporated herein by reference. Location data of the positioning system 208 and/or access port 12 may be determined by the tracking camera 213 by detection of the tracking markers 212 placed on or otherwise in fixed relation (e.g., in rigid connection) to any of the positioning system 208, the access port 12, the introducer 210, the tracked pointer 222 and/or other tracked instruments. The tracking marker(s) 212 may be active or passive markers. A display 206, 211 may provide an output of the computed data of the navigation system 205. In some examples, the output provided by the display 206, 211 may include axial, sagittal and coronal views of patient anatomy as part of a multi-view output.

The active or passive tracking markers 212 may be placed on tools (e.g., the access port 12 and/or the surgical microscope system 500) to be tracked, to determine the location and orientation of these tools using the tracking camera 213 and navigation system 205. The markers 212 may be captured by a stereo camera of the tracking system to give identifiable points for tracking the tools. A tracked tool may be defined by a grouping of markers 212, which may define a rigid body to the tracking system. This may in turn be used to determine the position and/or orientation in 3D of a tracked tool in a virtual space. The position and orientation of the tracked tool in 3D may be tracked in six degrees of freedom (e.g., x, y, z coordinates and pitch, yaw, roll rotations), in five degrees of freedom (e.g., x, y, z, coordinate and two degrees of free rotation), but preferably tracked in at least three degrees of freedom (e.g., tracking the position of the tip of a tool in at least x, y, z coordinates). In typical use with navigation systems, at least three markers 212 are provided on a tracked tool to define the tool in virtual space, however it is known to be advantageous for four or more markers 212 to be used.

Camera images capturing the markers 212 may be logged and tracked, by, for example, a closed circuit television (CCTV) camera. The markers 212 may be selected to enable or assist in segmentation in the captured images. For example, infrared (IR)-reflecting markers and an IR light source from the direction of the camera may be used. An example of such an apparatus may be tracking devices such as the Polaris® system available from Northern Digital Inc. In some examples, the spatial position and orientation of the tracked tool and/or the actual and desired position and orientation of the positioning system 208 may be determined by optical detection using a camera. The optical detection may be done using an optical camera, rendering the markers 212 optically visible.

Different tools and/or targets may be provided with respect to sets of markers 212 in different configurations. Differentiation of the different tools and/or targets and their corresponding virtual volumes may be possible based on the specification configuration and/or orientation of the different sets of markers 212 relative to one another, enabling each such tool and/or target to have a distinct individual identity defined within the navigation system 205. The individual identifiers may provide information to the system 205, such as information relating to the size and/or shape of the tool. The identifier may also provide additional information such as the tool's central point or the tool's central axis, among other information. The tool may also be determinable from a database of tools stored in or provided to the navigation system 205. The markers 212 may be tracked relative to a reference point or reference object in the operating room, such as the patient 202.

Various types of markers may be used. The markers 212 may all be the same type or may include a combination of two or more different types. Possible types of markers that could be used may include reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools they may be attached to. Reflective adhesives, structures and patterns, glass markers, and LED markers may be detectable using optical detectors, while RF and EM markers may be detectable using antennas. Different marker types may be selected to suit different operating conditions. For example, using EM and RF markers may enable tracking of tools without requiring a line-of-sight from a tracking camera to the markers 212, and using an optical tracking system may avoid additional noise from electrical emission and detection systems.

In some examples, the markers 212 may include printed or 3D designs that may be used for detection by an auxiliary camera, such as a wide-field camera (not shown) and/or the surgical microscope system 500. Printed markers may also be used as a calibration pattern, for example to provide distance information (e.g., 3D distance information) to an optical detector. Printed identification markers may include designs such as concentric circles with different ring spacing and/or different types of bar codes, among other designs. In some examples, in addition to or in place of using markers 212, the contours of known objects (e.g., the side of the access port 12) could be captured by and identified using optical imaging devices and the tracking system.

A guide clamp 218 (or more generally a guide) for holding the access port 12 may be provided. The guide clamp 218 may allow the access port 12 to be held at a fixed position and orientation while freeing up the surgeon's hands. An articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

In a surgical operating room (or theatre), setup of a navigation system may be relatively complicated; there may be many pieces of equipment associated with the surgical procedure, as well as elements of the navigation system 205. Further, setup time typically increases as more equipment is added. To assist in addressing this, the navigation system 205 may include two additional wide-field cameras (not shown) to enable video overlay information. Video overlay information can then be inserted into displayed images, such as images displayed on one or more of the displays 206, 211. The overlay information may illustrate the physical space where accuracy of the 3D tracking system (which is typically part of the navigation system) is greater, may illustrate the available range of motion of the positioning system 208 and/or the surgical microscope system 500, and/or may help to guide head and/or patient positioning.

In some examples, the tracking camera 213 may be part of any suitable tracking system. In some examples, the tracking camera 213 (and any associated tracking system that uses the tracking camera 213) may be replaced with any suitable tracking system which may or may not use camera-based tracking techniques. For example, a tracking system that does not use the tracking camera 213, such as a radiofrequency tracking system, may be used with the navigation system 205.

In some examples, the navigation system 205 may provide tools to the surgeon that may help to improve the performance of the medical procedure and/or post-operative outcomes. For example, the navigation system 205 may be used in medical procedures for removal of brain tumours and intracranial hemorrhages (ICH), a brain biopsy, a functional/deep-brain stimulation, a catheter/shunt placement procedure, open craniotomies, endonasal/skull-based/ENT, spine procedures, and in procedures related to other parts of the body such as spinal surgeries, breast biopsies, liver biopsies, etc. While several examples have been provided, examples of the present disclosure may be applied to any suitable medical procedure.

Figure 3:
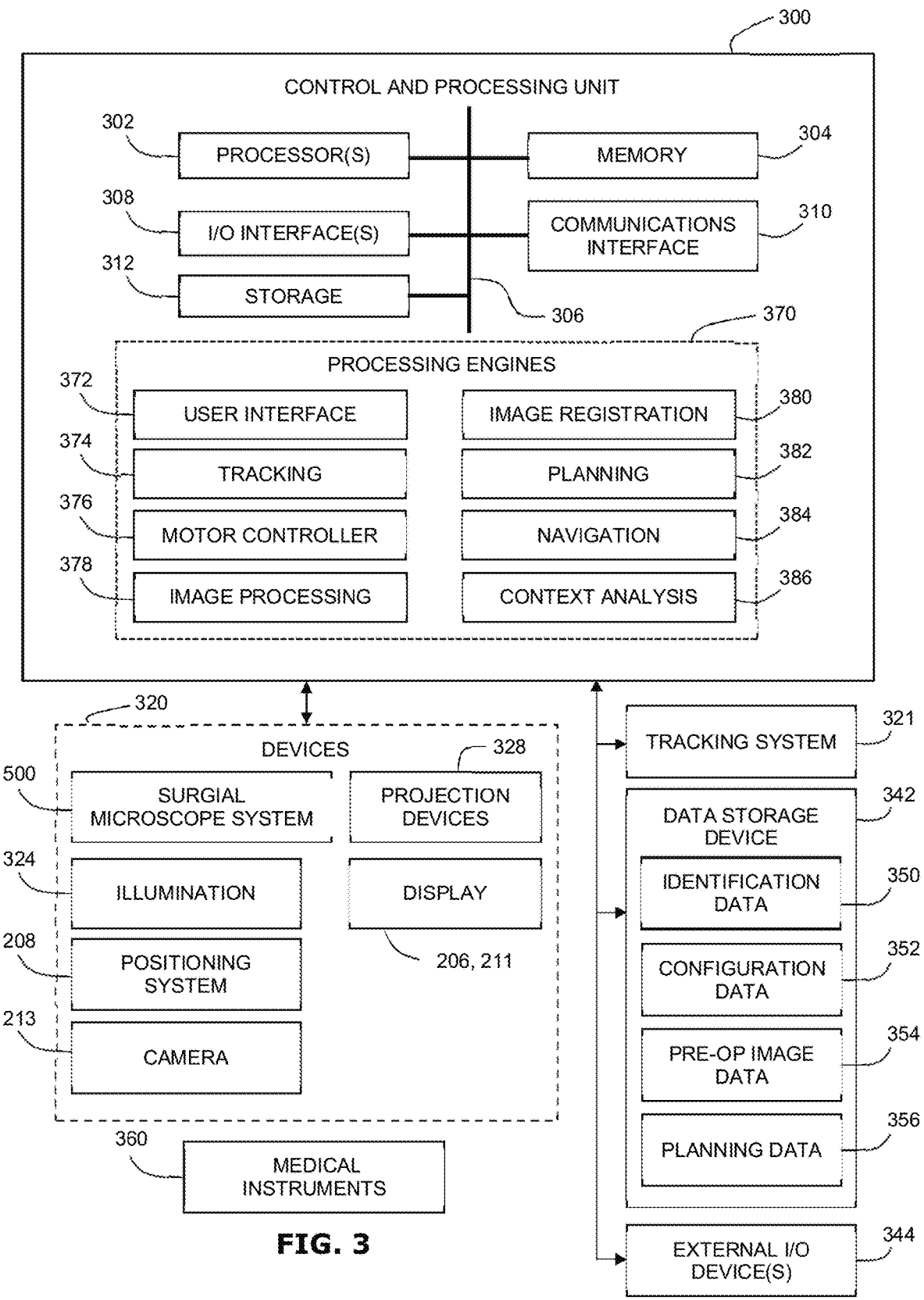
FIG. 3 is a block diagram illustrating an example control and processing system that may be used in an example navigation system.

FIG. 3 is a block diagram illustrating the control and processing system 300 that may be used in the medical navigation system 205 shown in FIG. 2 (e.g., as part of the equipment tower 207). As shown in FIG. 3, in one example, the control and processing system 300 may include one or more processors 302, a memory 304, a system bus 306, one or more input/output interfaces 308, a communications interface 310, and storage device 312. The control and processing system 300 may interface with external devices, such as a tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, the data storage device 342 may store identification data 350 for identifying one or more medical instruments 360 and configuration data 352 that associates customized configuration parameters with one or more medical instruments 360. The data storage device 342 may also store preoperative image data 354 and/or medical procedure planning data 356. Although the data storage device 342 is shown as a single device in FIG. 3, it will be understood that in other embodiments, the data storage device 342 may be provided as multiple storage devices.

The medical instruments 360 may be identifiable by the control and processing unit 300. The medical instruments 360 may be connected to and controlled by the control and processing unit 300, or the medical instruments 360 may be operated or otherwise employed independent of the control and processing unit 300. The tracking system 321 may be employed to track one or more medical instruments 360 and spatially register the one or more tracked medical instruments to an intraoperative reference frame. For example, the medical instruments 360 may include tracking markers 212 such as tracking spheres that may be trackable using the tracking camera 213. In another example, a sheath placed over a medical instrument 360 may provide tracking markers 212.

The control and processing unit 300 may interface with a number of devices 320. The devices 320 may include configurable devices, which may be preoperatively and/or intraoperatively reconfigured by the control and processing unit 300 (e.g., based on configuration parameters obtained from the configuration data 352). Examples of devices 320, as shown in FIG. 3, include the surgical microscope system 500, one or more illumination devices 324, the positioning system 208, the tracking camera 213, one or more projection devices 328, and one or more displays 206, 211.

Some or all functionalities described herein may be implemented using the control and processing unit 300. For example, the memory 304 may store instructions, as one or more processing modules or engines 370, executable by the processor(s) 302. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While example processing engines 370 are shown in FIG. 3, instructions may be stored in the memory 304 in any suitable form. In some examples, two or more of the processing engines 370 may be used together to perform a function. Although depicted as separately processing engines 370, the processing engines 370 370 may be embodied as a unified set of computer-readable instructions (e.g., stored in the memory 304) rather than distinct sets of instructions. In some examples, software instructions stored in the memory 304 may be used together with hardware logic implemented by the processor(s) 302. In some examples, functionalities disclosed herein may be implemented by the control and processing unit 300 in cooperation with another controller, such as a controller of the surgical microscope system 500, described further below.

It is to be understood that the system is not intended to be limited to the components shown in FIG. 3. One or more components of the control and processing system 300 may be provided as an external component or device. In one example, the navigation module 384 may be provided as an external navigation system that is integrated with the control and processing system 300.

Some embodiments may be implemented using the processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

Figure 4:
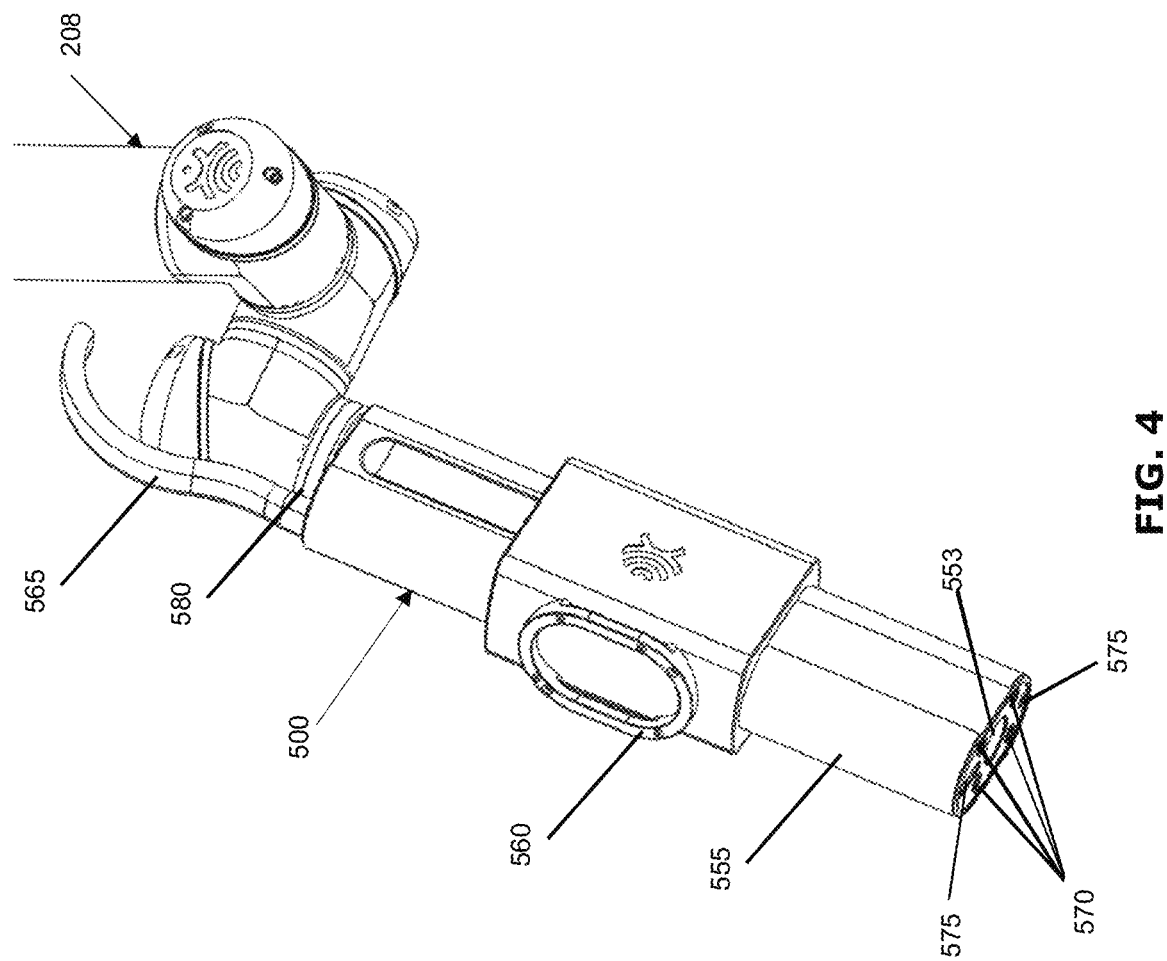
FIGS. 4 and 5 are different perspective views of an example surgical microscope system.
Figure 5:
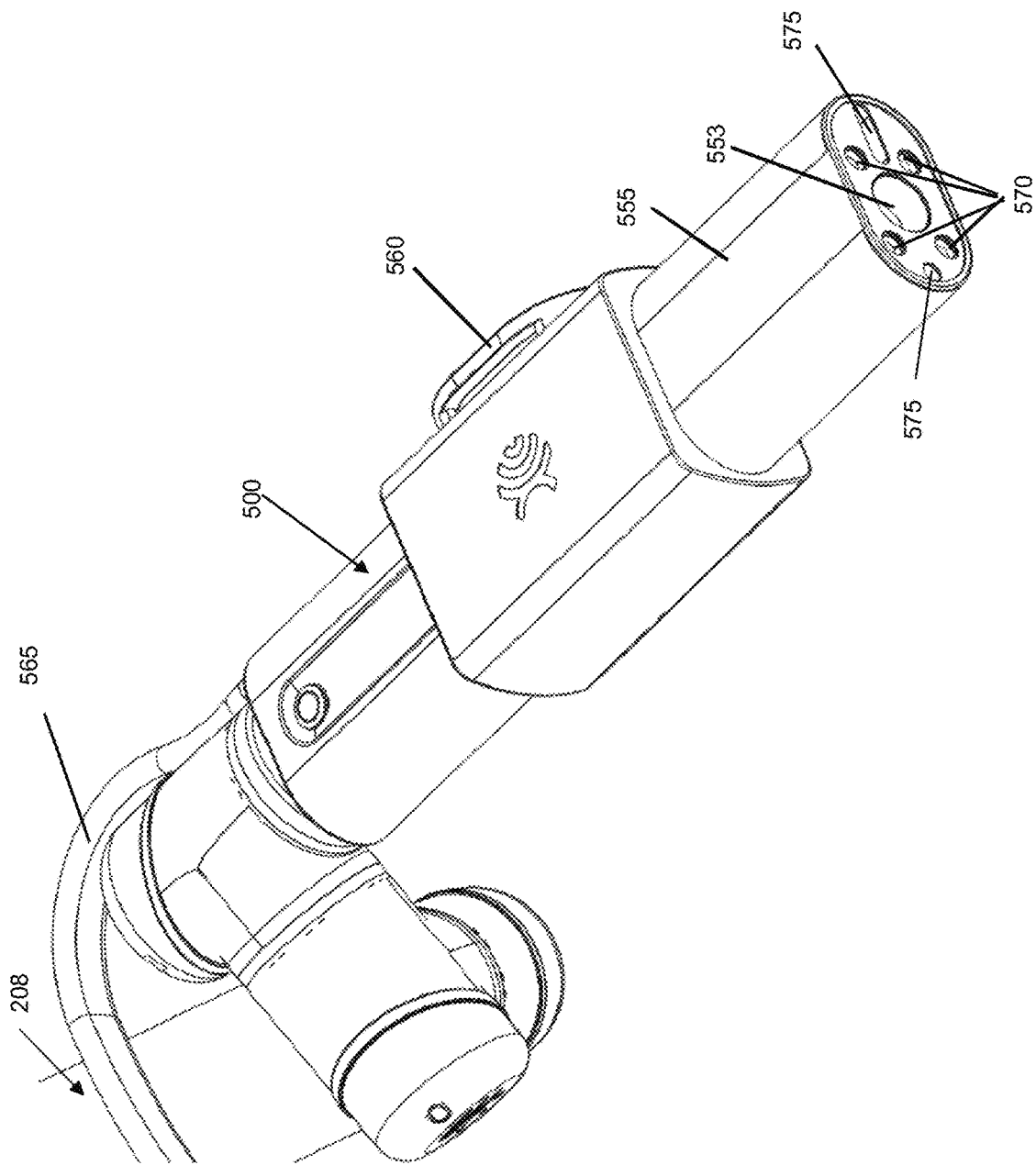

FIGS. 4 and 5 are perspective views of an example embodiment of the surgical microscope system 500. In this example, the surgical microscope system 500 is shown mounted to the positioning system 208 (e.g., at a distal end of a robotic arm). The surgical microscope system 500 is shown with a housing 555 that encloses the optical assembly, the camera and the controller, discussed further below with reference to FIG. 6. The housing 555 may be provided with a frame 560 on which trackable markers may be mounted, to enable tracking by the navigation system 205. The surgical microscope system 500 may communicates with the navigation system 205 via a cable 565 (shown partially cut off). The distal end of the surgical microscope system 500 may be provided with one or more light sources 570. The example shows four broad spectrum LEDs, however more or less light sources 570 may be used, of any suitable type. Although the light sources 570 are shown provided surrounding an aperture 553 of the surgical microscope system 500, in other examples the light source(s) 570 may be located elsewhere on the surgical microscope system 500. In some examples, the light source 570 may not itself generate light but rather direct light from another light generating component. For example, the light source 570 may be an output of a fibre optics cable connected to another light generating component, which may be part of the surgical microscope system 500 or external to the surgical microscope system 500. Providing the light source 570 with the surgical microscope system 500 may help to improve the consistency of image quality. In some examples, the power or output of the light source 570 may be controlled by the surgical microscope system 500 (e.g., by an internal controller) or may be controlled by a system external to the surgical microscope system 500 (e.g., by an external workstation or processor, such as a processor of a navigation system). The light source(s) 570 may be controlled to output different light spectra (e.g., fluorescence, UV or broad spectrum white light, depending on a selected mode of operation)

The distal end of the surgical microscope system 500 may also include one or more openings 575 for the cameras of an integrated 3D scanner. A support connector 580 for mounting the surgical microscope system 500 to the positioning system 208 is also shown.

Figure 6:
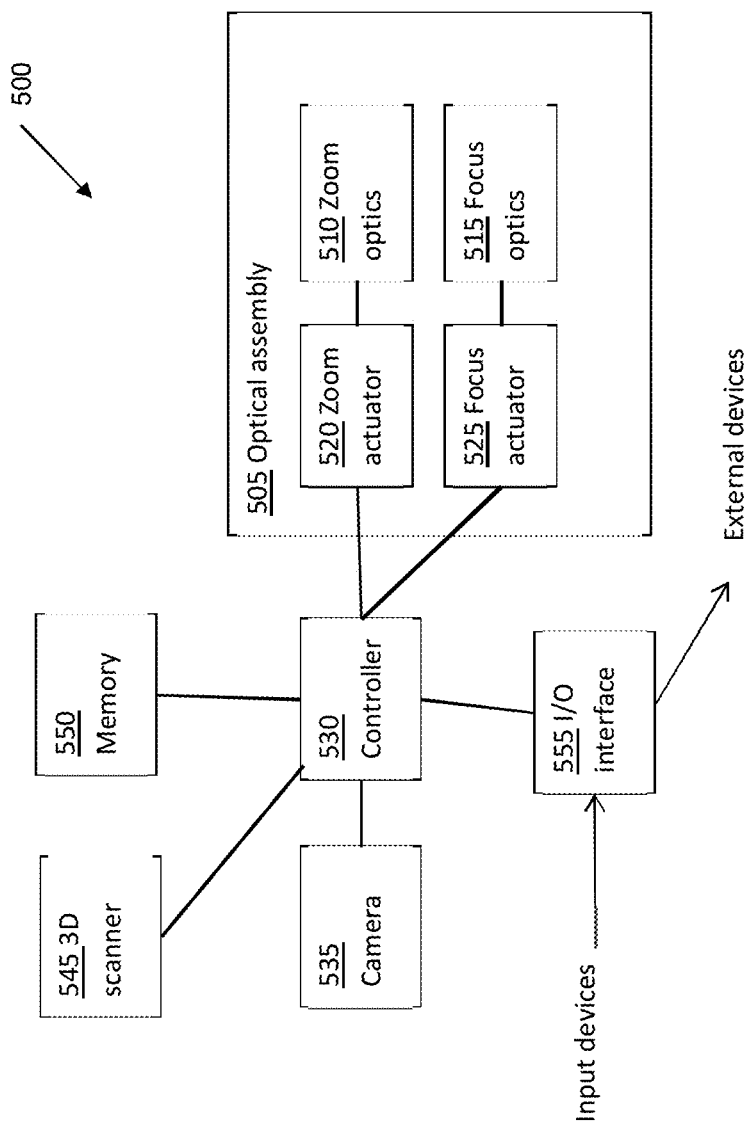
FIG. 6 is a block diagram of an example surgical microscope system.

FIG. 6 is a block diagram showing components of an example surgical microscope system 500. The surgical microscope system 500 may include an optical assembly 505 (also referred to as an optical train). The optical assembly 505 may include optics (e.g., lenses, optical fibers, etc.) for focusing and zooming on the viewing target. The optical assembly 505 may include zoom optics 510 (which may include one or more zoom lenses) and focus optics 515 (which may include one or more focus lenses). Each of the zoom optics 510 and focus optics 515 are and independently moveable within the optical assembly, in order to adjust the zoom and focus, respectively. Where the zoom optics 510 and/or the focus optics 515 include more than one lens, each individual lens may be independently moveable. The optical assembly 505 may include an aperture (not shown), which may be adjustable. The optical assembly 505 may include a zoom actuator 520 and a focus actuator 525 for positioning the zoom optics 510 and the focus optics 515, respectively. The zoom actuator 520 and/or the focus actuator 525 may be an electric motor, or other types of actuators including, for example, pneumatic actuators, hydraulic actuators, shape-changing materials (e.g., piezoelectric materials or other smart materials) or engines, among other possibilities. In some examples, the zoom actuator 520 and/or the focus actuator 525 may be implemented using a stepper motor and string-pulley drive system, for example as described in US Pat. Pub. No. 2006/0187562, the entirety of which is hereby incorporated by reference. The zoom optics 510 and zoom actuator 520 may be referred to together as motorized zoom. Similarly, the focus optics 515 and focus actuator 525 may be referred to together as motorized focus.

Although the term "motorized" is used in the present disclosure, it should be understood that the use of this term does not limit the present disclosure to use of motors necessarily, but is intended to cover all suitable actuators, including motors. Although the zoom actuator 520 and the focus actuator 525 are shown as part of the optical assembly 505, in some examples the zoom actuator 520 and the focus actuator 525 may be external to the optical assembly 505. The zoom actuator 520 and the focus actuator 525 may operate independently, to control positioning of the zoom optics 510 and the focus optics 515, respectively. The lens(es) of the zoom optics 510 and/or the focus optics 515 may be each mounted on a linear stage (e.g., a motion system that restricts an object to move in a single axis, which may include a linear guide and an actuator; or a conveyor system such as a conveyor belt mechanism) that is moved along a set of rails by the zoom actuator 520 and/or the focus actuator 525, respectively, to control positioning of the zoom optics 510 and/or the focus optics 515. In some examples, the zoom optics 510 and/or the focus optics 515 may be moved or actuated without the use of the zoom actuator 520 and/or the focus actuator 525. For example, the focus optics 515 may use electrically-tunable lenses or other deformable material that may be controlled directly by the controller 530.

The independent operation of the zoom actuator 520 and the focus actuator 525 may enable the zoom and focus to be adjusted independently. Thus, when an image is in focus, the zoom may be adjusted without requiring further adjustments to the focus optics 515 to produce a focused image.

Operation of the zoom actuator 520 and the focus actuator 525 may be controlled by a controller 530 (e.g., a microprocessor) of the surgical microscope system 500. The controller 530 may receive control input (e.g., from an external system, such as an external processor or an input device). Where the surgical microscope system 500 is used as part of the navigation system 205, the controller 530 may communicate with and receive control input from a processor (e.g., in the control and processing unit 300) of the navigation system 205. The control input may indicate a desired zoom and/or focus, and the controller 530 may in response control the zoom actuator 520 and/of focus actuator 525 to move the zoom optics 510 and/or the focus optics 515 accordingly to achieve the desired zoom and/or focus. In other examples, the controller 530 may determine the desired zoom and/or focus and control the optical assembly 505 without instructions from an external controller.

The optical assembly 505 may also include one or more auxiliary optics (not shown) such as a filter wheel for selecting an optical filter for imaging. The filter wheel may hold one or more optical filters, for example an optical filter for fluorescence imaging. The filter wheel may also be motorized and may be controlled by the controller 530, to place a selected optical filter in the optical path.

The surgical microscope system 500 may also include a camera 535 (e.g., a high-definition (HD) camera) that captures image data from the optical assembly. Operation of the camera may be controlled by the controller 530. The camera 535 may also output data to an external system (e.g., an external workstation or external output device) to view the captured image data. In some examples, the camera 535 may output data to the controller 530, which in turn transmits the data to an external system for viewing. By providing image data to an external system for viewing, the captured images may be viewed on a larger display and may be displayed together with other information relevant to the medical procedure, including navigational information (e.g., a wide-field view of the surgical site, navigation markers, 3D images, etc.). Providing the camera 535 with the surgical microscope system 500 may help to improve the consistency of image quality among different medical centers. In some examples, the surgical microscope system 500 may include more than one camera 535. For example, the surgical microscope system 500 may include two cameras 535, which may cooperate to obtain stereoscopic image data. In general, the surgical microscope system 500 may include one or more cameras 535. For simplicity the description below will refer to the camera 535 in the singular, however this is not intended to be limiting.

Image data captured by the camera 535 may be displayed on a display together with a wide-field view of the surgical site, for example in a multiple-view user interface. The portion of the surgical site that is captured by the camera 535 may be visually indicated in the wide-field view of the surgical site.

The surgical microscopy system 500 may include an I/O interface 555, to enable the controller 530 to receive input from and/or send output to one or more external devices. For example, the controller 530 may receive user input from one or more input devices (e.g., a voice recognition input system, a foot pedal or an external workstation providing a user interface) via the I/O interface 555. The controller 530 may also provide communicate with external devices, such as the positioning system 208 (e.g., to adjust the working distance and/or move the surgical microscope system 500), the display 206, 211 (e.g., to display captured images and/or control display settings) and/or the navigation system 205 via the I/O interface 555.

By providing the controller 530, the zoom actuator 520 and the focus actuator 525 all as part of the surgical microscope system 500, the surgical microscope system 500 may enable an operator (e.g., a surgeon) to control zoom and/or focus during a medical procedure without having to manually adjust the zoom and/or focus optics 510, 515. In some examples, the controller 530 may carry out preset instructions to maintain the zoom and/or focus at preset values (e.g., according to a selected mode of operation) without requiring continuous control input during the medical procedure.

In some examples, an external processor (e.g., a processor of a workstation or the navigation system 205) in communication with the controller 530 may be used to provide control input to the controller 530. For example, the external processor may provide a graphical user interface via which the operator or an assistant may input instructions to control zoom and/or focus of the surgical microscope system 500. In some examples, the surgical microscope system 500 may be partially or entirely controlled by an external controller (e.g., by the control and processing unit 300 of the navigation system 205). For example, the controller 530 of the surgical microscope system 500 may receive control instructions from an external controller. In another example, the controller 530 may be omitted and the surgical microscope system 500 may communicate with an external controller to receive control instructions. The controller 530 may alternatively or additionally be in communication with an external input system (e.g., a voice recognition input system or a foot pedal).

The surgical microscope system 500 may include a three-dimensional (3D) scanner 545 or 3D camera for obtaining 3D information of the viewing target. 3D information from the 3D scanner 545 may also be captured by the camera 535, or may be captured by the 3D scanner 545 itself. Operation of the 3D scanner 545 may be controlled by the controller 530, and the 3D scanner 545 may transmit data to the controller 530. In some examples, the 3D scanner 545 may itself transmit data to an external system (e.g., an external work station). 3D information from the 3D scanner 545 may be used to generate a 3D image of the viewing target (e.g., a 3D image of a target tumor to be resected). 3D information may also be useful in an augmented reality (AR) display provided by an external system. For example an AR display (e.g., provided via AR glasses) may, using information from a navigation system to register 3D information with optical images, overlay a 3D image of a target specimen on a real-time optical image (e.g., an optical image captured by the camera 535).

The controller 530 may be coupled to a memory 550. The memory 550 may be internal or external of the surgical microscope system 500. Data received by the controller 530 (e.g., image data from the camera 535 and/or 3D data from the 3D scanner) may be stored in the memory 550. The memory 550 may also contain instructions to enable the controller to control the optical assembly 505. For example, the memory 550 may store instructions to enable the controller to control the optical assembly 505 according to different modes of operation, as discussed further below.

The surgical microscope system 500 may communicate with an external system (e.g., a navigation system or a workstation) via wired or wireless communication. In some examples, the surgical microscope system 500 may include a wireless transceiver (not shown) to enable wireless communication.

In some examples, the surgical microscope system 500 may include a power source (e.g., a battery) or a connector to a power source (e.g., an AC adaptor). In some examples, the surgical microscope system 500 may receive power via a connection to an external system (e.g., an external workstation or processor).

In some examples, the surgical microscope system 500 may also provide mechanisms to enable manual adjusting of the zoom and/or focus optics 510, 515, similarly to conventional systems. Such manual adjusting may be enabled in addition to motorized adjusting of zoom and focus. In some examples, such manual adjusting may be enabled in response to user selection of a "manual mode" on a user interface.

The surgical microscope system 500 may be mountable on a moveable support structure, such as the positioning system (e.g., robotic arm) of a navigation system, a manually operated support arm, a ceiling mounted support, a moveable frame, or other such support structure. The surgical microscope system 500 may be removably mounted on the moveable support structure. In some examples, the surgical microscope system 500 may include a support connector (e.g., a mechanical coupling) to enable the surgical microscope system 500 to be quickly and easily mounted or dismounted from the support structure. The support connector on the surgical microscope system 500 may be configured to be suitable for connecting with a typical complementary connector on the support structure (e.g., as designed for typical end effectors). In some examples, the surgical microscope system 500 may be mounted to the support structure together with other end effectors, or may be mounted to the support structure via another end effector.

When mounted, the surgical microscope system 500 may be at a known fixed position and orientation relative to the support structure (e.g., by calibrating the position and orientation of the surgical microscope system 500 after mounting). In this way, by determining the position and orientation of the support structure (e.g., using a navigation system or by tracking the movement of the support structure from a known starting point), the position and orientation of the surgical microscope system 500 may also be determined. In some examples, the surgical microscope system 500 may include a manual release button that, when actuated, enable the surgical microscope system 500 to be manually positioned (e.g., without software control by the support structure).

In some examples, where the surgical microscope system 500 is intended to be used in a navigation system environment, the surgical microscope system 500 may include an array of trackable markers, which may be mounted on a frame on the surgical microscope system 500) to enable the navigation system to track the position and orientation of the surgical microscope system 500. Alternatively or additionally, the moveable support structure (e.g., a positioning system of the navigation system) on which the surgical microscope system 500 is mounted may be tracked by the navigation system and the position and orientation of the surgical microscope system 500 may be determined using the known position and orientation of the surgical microscope system 500 relative to the moveable support structure.

The trackable markers may include passive reflective tracking spheres, active infrared (IR) markers, active light emitting diodes (LEDs), a graphical pattern, or a combination thereof. There may be at least three trackable markers provided on a frame to enable tracking of position and orientation. In some examples, there may be four passive reflective tracking spheres coupled to the frame. While some specific examples of the type and number of trackable markers have been given, any suitable trackable marker and configuration may be used, as appropriate.

Determination of the position and orientation of the surgical microscope system 500 relative to the viewing target may be performed by a processor external to the surgical microscope system 500 (e.g., a processor of the navigation system). Information about the position and orientation of the surgical microscope system 500 may be used, together with a robotic positioning system, to maintain alignment of the surgical microscope system 500 with the viewing target (e.g., to view down an access port during port-based surgery) throughout the medical procedure.

For example, the navigation system may track the position and orientation of the positioning system and/or the surgical microscope system 500 either collectively or independently. Using this information as well as tracking of the access port, the navigation system may determine the desired joint positions for the positioning system so as to maneuver the surgical microscope system 500 to the appropriate position and orientation to maintain alignment with the viewing target (e.g., the longitudinal axes of the surgical microscope system 500 and the access port being aligned). This alignment may be maintained throughout the medical procedure automatically, without requiring explicit control input. In some examples, the operator may be able to manually move the positioning system and/or the surgical microscope system 500 (e.g., after actuation of a manual release button). During such manual movement, the navigation system may continue to track the position and orientation of the positioning system and/or the surgical microscope system 500. After completion of manual movement, the navigation system may (e.g., in response to user input, such as using a foot pedal, indicating that manual movement is complete) reposition and reorient the positioning system and the surgical microscope system 500 to regain alignment with the access port.

The working distance may be determined by the controller 530 using information (e.g., received from the navigation system, from the positioning system or other external system) about the position and orientation of the surgical microscope system 500 and/or the positioning system relative to the viewing target. In some examples, the working distance may be determined by the controller 530 using an infrared light (not shown) mounted on near the distal end of the surgical microscope system 500.

The surgical microscope system 500 may be used to automatically control the optical assembly 505 and/or other aspects of the captured image according to a selected mode of operation. In a medical procedure, it is common for a surgeon to prefer different magnification and/or focus settings at different phases of the procedure. For example, during a tumor removal step of a tumor removal procedure, the surgeon is likely to want to focus the tumor in the center of the captured image. In another example, during tumor removal using fluorescence, the surgeon would likely want to focus at the area where fluorescence is displayed. There may also be situations where the procedure enters an abnormal phase or emergency phase outside of the planned procedure phases, such as when bleeding occurs.

Figure 7:
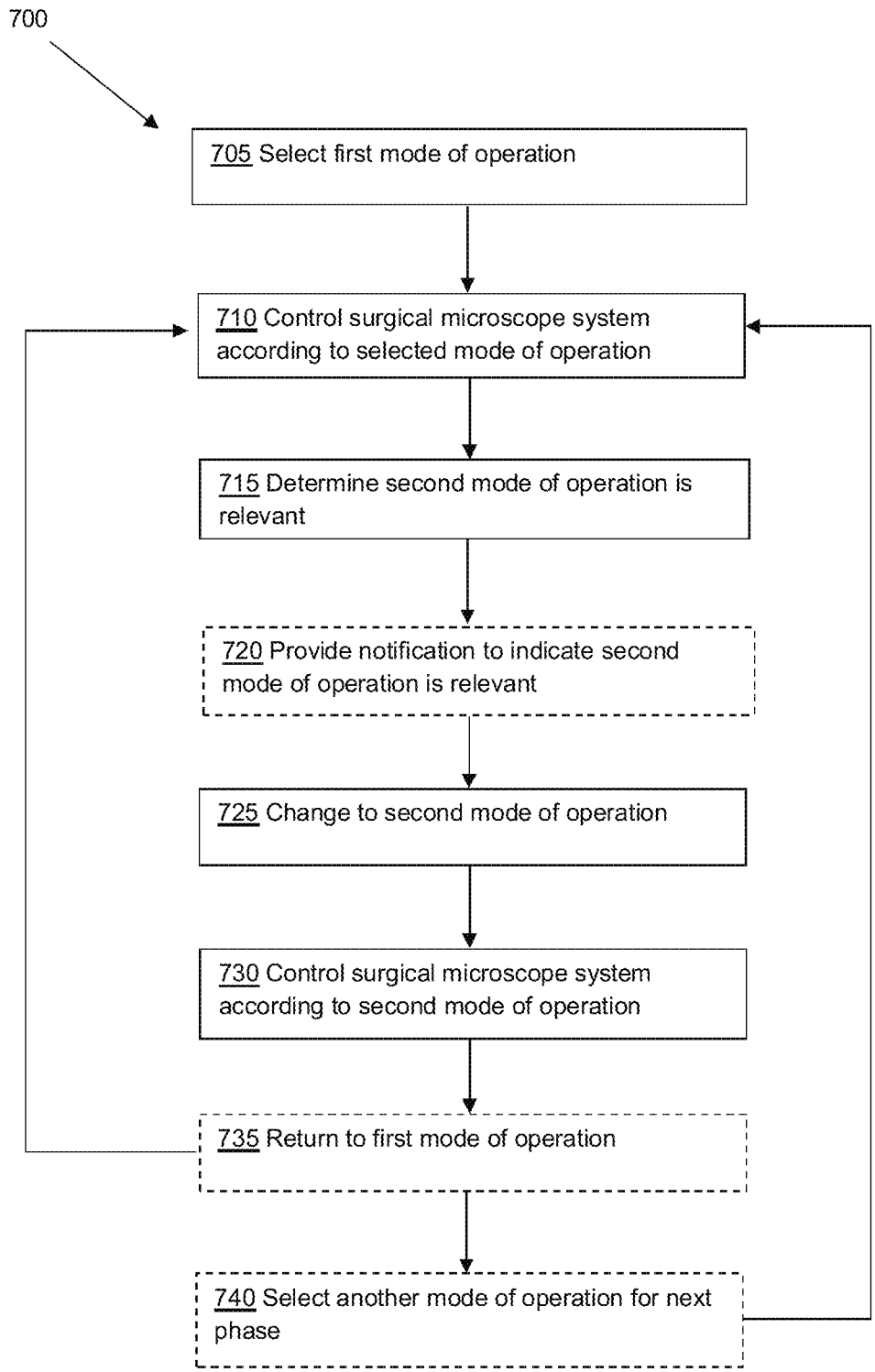
FIG. 7 is a flow chart illustrating an example method for controlling an example surgical microscope system.

FIG. 7 is a flowchart illustrating an example method 700 for operation of the surgical microscope system 500 under different modes of operation.

At 705, a first mode of operation is set to be the selected mode of operation. Selection of the first mode of operation may be based on user input (e.g., voice input or via a user interface presented on a display), such as input identifying the type of medical procedure (e.g., selected from a drop-down menu) and/or input identifying the surgeon performing the procedure. Selection of the first mode of operation may additionally be based on user input identifying the phase of the medical procedure (e.g., identification of the surgical task to be performed).

The first mode of operation may be one of a plurality of available modes of operation that each define one or more settings (e.g., magnification and/or focus depth) for the surgical microscope system. Each available mode of operation may correspond to at least one phase of a medical procedure. A given mode of operation may be relevant to only one type of medical procedure (e.g., tumor removal mode may be relevant only to tumor removal procedures), may be relevant to multiple types of medical procedures (e.g., wide view mode may be relevant to different surgical procedures), may be relevant to only one phase of a medical procedure (e.g., fluorescence mode may be relevant only to a fluorescence-guided phase) or may be relevant to different phases of a medical procedure (e.g., wide view mode may be relevant for both surgical site opening and surgical site closing phases).

Operation under a selected mode of operation may control other settings of the surgical microscope system, in addition to or instead of control of the optical assembly. For example, where the surgical microscope system includes a light source and/or a filter wheel, the selected mode of operation may define a setting for the illumination, light spectra and/or optical filter to be used when capturing an image.

Operation under a selected mode of operation may control not only operation of the surgical microscope system, but additionally or alternatively may control external devices relevant to the capture and display of images. For example, a selected mode of operation may define settings for external devices such as a positioning system with robotic arm supporting the surgical microscope system and/or a display displaying the captured image. For example, the selected mode of operation may define a working distance between the surgical microscope system and the surgical site, and the surgical microscope system may send control signals to the positioning system to position the base of the positioning system and/or the joints of the robotic arm in order to maintain the supported surgical microscope system at the defined working distance. Control of the positioning system may also be used to maintain a certain region of the captured image in focus. Control of the positioning system (e.g., robotic arm and/or microscope base) may also be used to position the field-of-view of the surgical microscope system with respect to the region of operation. For example, if the surgeon prefers to operate near the upper right-hand corner instead of the center of the image, the surgical microscope system may be positioned so that the interested region of operation is at the upper right-hand corner of the microscope view. Furthermore, control of the positioning system may be used to help set the preferred distance and/or orientation of the microscope with respect to the patient, bed and/or other surgical equipment in the operating room, for example in order to improve space available for the surgeon(s) and/or workflow for the procedure. Data from one or more additional cameras capturing the surrounding environment of the operating room may also be included as part of the log or data, which may be analyzed to determine and/or improve positioning of the positioning system (e.g., robotic arm and/or microscope base). The selected mode of operation may also define display settings for the display, such as color settings (e.g., color correction, color enhancement and/or color balance), contrast and/or brightness, and/or may control the display to display an additional picture-in-picture image, for example.

A mode of operation may define one or more settings based on historical usage of the surgical microscope system. For example, the controller of the surgical microscope system, or an external processor (e.g., in a separate workstation) may analyze historical usage logs stored in an external or internal database, in order to determine the most common or most appropriate settings for a given phase within a given type of medical procedure. Such analysis of historical usage may be performed using a nearest neighbour algorithm, or more advanced machine learning techniques, for example. Such analysis may be continuously updated as usage logs are added to the database, with the result that the settings defined in the mode of operation may change over time (e.g., to reflect up-to-date medical practice) without requiring direct user input. The update may continue until the user is satisfied with the settings (e.g., indicated by the user continuously using the settings without making manual adjustments), or until settings are optimized (e.g., indicated by new log data that does not change the settings). The log of the surgical microscope system may include records of, for example, zoom setting, focus setting, working distance, colour settings, camera settings, position of the positioning system, modes of operation, user inputs, errors, settings of the video processors, tracking, light source, images and/or video footages captured, and may also indicate the date, time and/or duration of the settings and changes made in the system. For example, the surgical system may define the settings based on which setting has the longest usage duration in each phase and/or which setting has the greater usage among different surgeries. Any manual adjustment logged may be counted as a change to the setting, and the system may automatically update the setting to reflect the manual adjustment if the same manual adjustment is made numerous times for the same phase. In some examples, historical usage may include previous usage of the surgical microscope system within the same session or procedure as the current usage. That is, analysis of usage may be performed even during a procedure, such that settings may be updated throughout the procedure based on previous usage of the surgical microscope system during that same procedure. In addition, multiple machine learning algorithms could be utilized to define settings. It should be noted certain settings recorded in historical usage logs may be specific to a particular scenario in a procedure. An automatic machine learning algorithm may select the most relevant historical usage data from the log (e.g., based on comparison of captured images of the current procedure with captured images stored in the historical usage logs) to determine the appropriate settings. The surgical microscope system may also apply multiple machine learning algorithms to the historical usage data in order to define appropriate settings for each mode of operation, in each phase of each medical procedure.

A mode of operation may define one or more user-specific settings, if the user provides input indicating the specific surgeon performing the medical procedure. A user-specific setting may be based on user-inputted preference (e.g., a given surgeon may provide input specifying a brighter displayed image, or a certain amount of parallax for a 3D display) or based on user-specific historical usage (e.g., analysis of historical usage logs may automatically determine that a given surgeon always uses a brighter display).

A mode of operation may be an initial training mode, in which the user selects the desired settings. The user-selected settings may be stored in the usage log and may serve as the basis for subsequent analysis of historical usage.

At 710, the surgical microscope system is controlled using the selected mode of operation. For example, the optical assembly may be controlled to adjust the optics (e.g., mechanically or electrically control focus and/or zoom lenses, for example using the focus and/or zoom actuator) in order to achieve a magnification and/or focus depth according to settings defined in the first mode of operation. It should be understood that other settings for components internal or external to the surgical microscope system may be similarly controlled according to the selected mode of operation. Where a setting is defined for an external component, the surgical microscope system may send control instructions to directly control the external component or to an external processor that in turn controls the external component.

At 715, while the surgical microscope system is operating under the selected first mode of operation, a determination is made that a different second mode of operation is relevant. This determination may be made based on the image captured by the surgical microscope system, for example based on detection of an indicator in the captured image. For example, in any mode of operation, the surgical microscope may automatically and continuously perform image analysis on the captured image to detect certain indicators that may indicate the second mode of operation is relevant.

The second mode of operation may correspond to an abnormal phase or emergency phase of the procedure. For example, if the surgical microscope system determines that the captured image contains a high proportion or largely increasing proportion of red pixels, this may be an indicator that there is bleeding in the surgical site and an emergency "bleeding" mode of operation is relevant. Other abnormal or emergency phases that may be detected by the surgical microscope system (e.g., using appropriate image analysis techniques) include, for example, ballooning of a vessel, tremor, seizure, hemorrhage, blood clot, brain swelling, impairment (e.g., to speed, vision, coordination or balance), skull fracture, stroke, fluid build up or infection, among others.

Optionally, at 720, the surgical microscope system causes a notification to be provided to the surgeon to indicate that the second mode of operation is relevant. The notification may be provided via any suitable output mechanism, such as an audio output, tactile output and/or visual output. The notification may inform the surgeon that an abnormal or emergency phase has been detected, and may provide the surgeon an option to confirm or dismiss the notification.

In some examples, providing the notification may include changing the display to include a visual notification of the possible emergency, and further include a picture-in-picture display with an inset showing a magnified view of the region where the emergency indicator (e.g., bleeding) was detected. In some examples, the picture-in-picture display may be an enlarged view of the current real-time captured video image, an enlarged view of a captured static image, or an enlarged view of a short video recording, among other possibilities.

At 725, the selected mode of operation is changed to the second mode of operation. If a notification was provided at 720, the change to the second mode of operation may occur only after the surgeon provides confirmation (e.g., via voice input or other input mechanism) to change to the second mode of operation.

The second mode of operation may define a setting that enhances viewing of a region relevant to the abnormal or emergency phase. For example, the second mode of operation may define a higher magnification and focus region that focuses on an area where bleeding has been detected.

At 730, the surgical microscope system is then controlled according to the selected second mode of operation. For example, the optical assembly may be controlled to adjust the optics (e.g., mechanically or electrically control focus and/or zoom lenses) in order to achieve a magnification and/or focus depth according to settings defined in the second mode of operation. It should be understood that other settings for components internal or external to the surgical microscope system may be similarly controlled according to the selected mode of operation. For example, the surgical microscopy system may output control signals that controls the display to display a picture-in-picture static or video image that focuses on the bleeding site.

Optionally, at 735, the selected mode of operation returns to the first mode of operation, and the surgical microscopy system returns to control using the setting(s) defined in the first mode of operation at 710. This can occur, for example, when the user provides input indicating that the second mode of operation is no longer relevant, or when the indicator of the abnormal or emergency phase is no longer detected in the captured image. In some examples, 735 may be omitted, such as where the surgeon immediately proceeds to the next phase of the medical procedure instead.

Optionally, at 740, another mode of operation is selected, and the surgical microscopy system is controlled using the setting(s) defined in the new selected mode of operation at 710. For example, the phase associated with the first mode of operation may be completed and the surgeon may provide input (e.g., voice input or selection via a user interface) indicating the next phase in the medical procedure. Another mode of operation may then be selected according to the indicated next phase in the medical procedure. In some examples, 740 may be omitted, such as where the surgical microscope system is not needed for the next phase of the medical procedure.

Some example modes of operation are now described. It should be understood that the modes described below are provided as examples only and are not intended to be limiting. Further, settings of different modes may be combined, and may be configurable.

A mode of operation may define a region of focus in the captured image, so that conventional autofocus features can be utilized within a much smaller region to determine the focus. For example, a "wide view" mode may control the surgical microscope system to perform autofocus only on the central 30% of the captured image. A "fluorescence" mode may control the surgical microscope system to detect the location of fluorescence in the captured image and perform autofocus in the region of fluorescence. Under "fluorescence" mode, the surgical microscope system may further control a light source to provide fluorescent light and/or control an optical filter to enhance viewing of the fluorescence. Similar control may be provided by a "UV" mode, for example. A "tool tracking" mode may control the surgical microscope system to perform autofocus on a region that is indicated by a tracked tool or laser pointer. The surgical microscope system may communicate with a tracking system (which may track a tool using trackable markers coupled to the tool) to receive tracking information in order to properly autofocus on the indicated region.

In each mode of operation, an option may be provided to enable the surgeon to change the settings and/or manually control the magnification and/or focus. Such changes may be recorded in a usage log and this historical usage data may be used to refine the mode of operation, for example using machine learning techniques. Under manual control, the focus region may be switched by traversing through all available planes of focus until the desired focus region is reached. A "semi-manual control" mode may also be provided in which different focus regions are determined by the surgical microscope system (e.g., based on potential features of interest in the captured image, which may be identified based on a preoperative treatment plan or based on machine learning algorithms) and the surgeon is able to manually select among the focus regions provided. For example, a preoperative treatment plan may include identification of regions of interest that may be loaded into the surgical microscope system.

In some examples, in which there may be multiple regions of interest for focusing, the surgical microscope system may automatically select one region of interest to perform auto-focusing, for example based on surgeon-specific preference determined from historical usage logs.

The modes of operation that are available may be tailored for a given medical procedure. For example, after providing input identifying the type of medical procedure, only a subset of all available modes of operation may be available for use during that medical procedure.

For user-specific settings, it may be necessary for the surgeon performing a medical procedure be identified both during the current medical procedure and in usage logs. For example, a surgeon who likes to operate with certain field-of-view and magnification for certain tasks as well as certain position of the robotic arm may have such preferences logged in the historical usage logs. The modes of operation specific to this surgeon may accordingly define settings according to the surgeon's personal preference at each phase of the medical procedure, under a "surgical assistant" mode. User-specific settings may include, for example, the amount of parallax preferred by the specific surgeon, for viewing a 3D display. The parallax setting may further be automatically adjusted according to the type of medical procedure and/or length of the procedure.

In an "initial setup" mode, after the specific medical procedure has been inputted (and any initial calibration may be performed), the surgical microscope system may automatically control the positioning of robotic arm and/or positioning of the base of the positioning system to set the correct distance and orientation of the microscope base from the surgical bed, working distance and/or viewing orientation, and control the optical assembly to set the correct magnification and/or focus with respect to the surgical opening, so that the overall system is ready for start of the procedure, with minimal manual setup required. In addition, the surgical microscope system might automatically set the initial settings (e.g., camera settings, color settings and/or video recording setting, among others) preferred by a specific surgeon for the specific surgery being performed.

In any of the modes of operation, the surgical microscope system may also operate in an "automatic surveillance" mode, in which the surgical microscope continuously or periodically analyzes the captured image (e.g., in real-time or near real-time) to determine the possibility of an abnormal or emergency phase. When a risk is identified, a notification may be provided, such as a visual notification (e.g., an inset static or video image showing the area of the risk) displayed on the display. The notification may include options for the surgeon to proceed with suggested actions on the identified risk. For example, if damage is made to vessels during a tumor removal step and caused excessive blood, the surgical microscope system may identify the presence of excessive blood by detecting the saturation of red starting from a specific region of the image in a short period of time. The surgical microscope system may then control the display to display a notification showing the identified bleeding site. The surgeon may be provided with an option to change the mode of operation from "tumor removal" to "bleeding" mode. In the "bleeding" mode, the defined settings may include magnification, focus, working distance, camera and color settings, as well as position of the positioning system, that are more suitable for stopping the bleeding. The surgeon may also be provided with an option to dismiss the notification and remain in "tumor removal" mode.

Figure 8A:
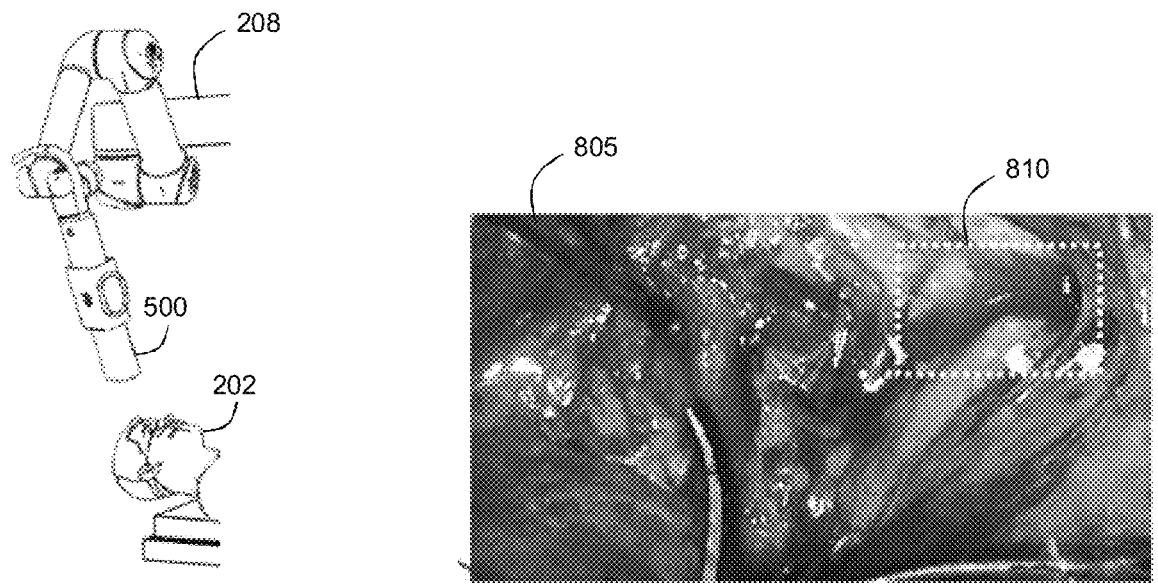
FIGS. 8A and 8B illustrate an example of a switch in mode of operation for the surgical microscope system.
Figure 8B:
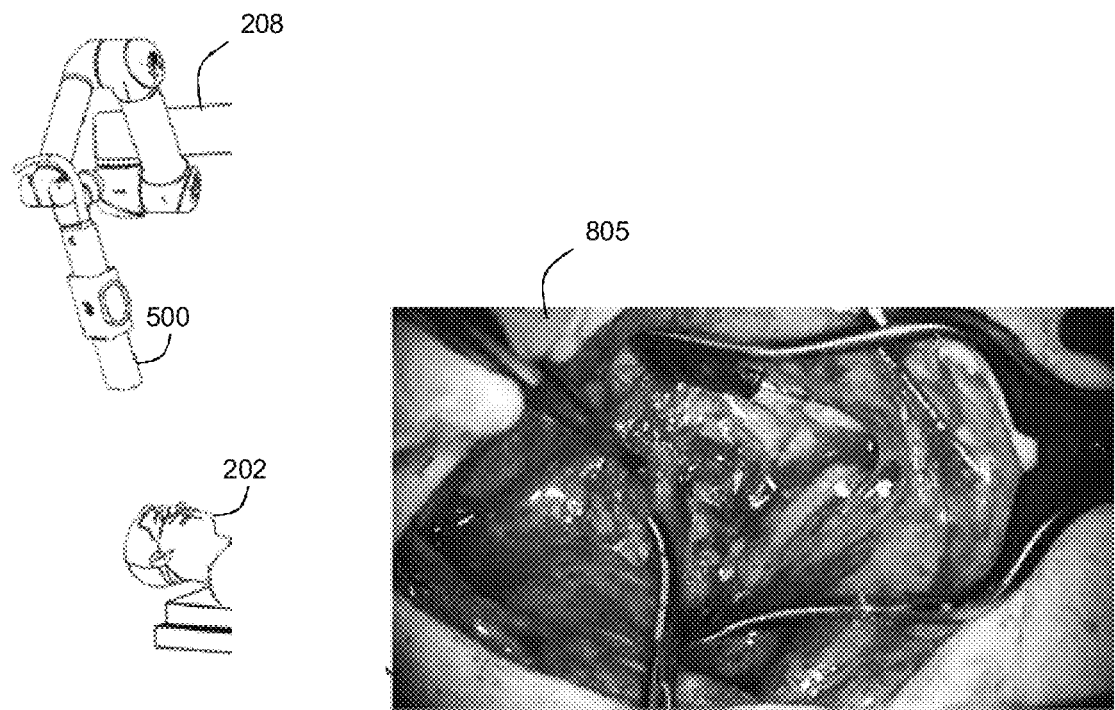

FIGS. 8A and 8B illustrate an example of how the surgical microscope system may change to a "bleeding" mode of operation. In FIG. 8A, the surgical microscope system is operating in the "tumor removal" mode. The surgical microscope system 500 controls the positioning system 208 to have a short working distance to the patient 202. The captured image 805 shows the surgical site in a high magnification, with a focus on the target tumor. By continuously analyzing the image, the surgical microscope system 500 may identify an indicator of bleeding in a region of the image. The surgical microscope system 500 may provide a notification that "bleeding" mode may be relevant. The notification may be displayed as an outline 810 showing where bleeding has been detected in the image. The surgeon may additionally be provided with an option to confirm the change to "bleeding" mode of operation. In FIG. 8B, the surgical microscope system has switched to the "bleeding" mode of operation. In this mode of operation, the positioning system 208 is controlled to have a longer working distance, and the optical assembly is controlled to achieve a lower magnification and a focus on the bleeding region. In other examples, in "bleeding" mode, the setting may increase magnification so that the region identified as having bleeding (i.e., the outlined area in FIG. 8A) fills the displayed image. In some examples, the surgeon may be provided with options to magnify the bleeding region in the displayed image, display the bleeding region in a secondary display, or magnify a live view of the bleeding region while maintaining an inset static image of the larger surgical site, among other options.

As noted above, the surgical microscope system 500 may be used together with or as part of a navigation system 205, which can provide tracking of the surgical microscope system 500, surgical site, patient, medical tools and/or positioning system 208, for example. The surgical microscope system 500 may also access or receive information from an external workstation or memory storing a pre-operating navigation plan. Accordingly, the surgical microscope system 500 may have access to information such as location of surgical opening, location of tool tip, location of tumor, planned surgical path and/or current working distance. In addition, the surgical microscope system 500 may extract information from the captured image (e.g., using image processing). Furthermore, the surgical microscope system 500 may extract information from the positioning system 208, such as force applied to the positioning system 208 or other object sensor (e.g., force/pressure sensor, thermal/temperature sensor, proximity sensor, Light Detection and Ranging (LIDAR) sensor, optical sensors, IR sensor, ultrasonic sensor, motion sensor and/or accelerometer). This information, which may be from multiple sources, may be used to control operation of the surgical microscope system 500 (and other external systems where appropriate) according to setting(s) defined in the selected mode of operation.

Figure 9:
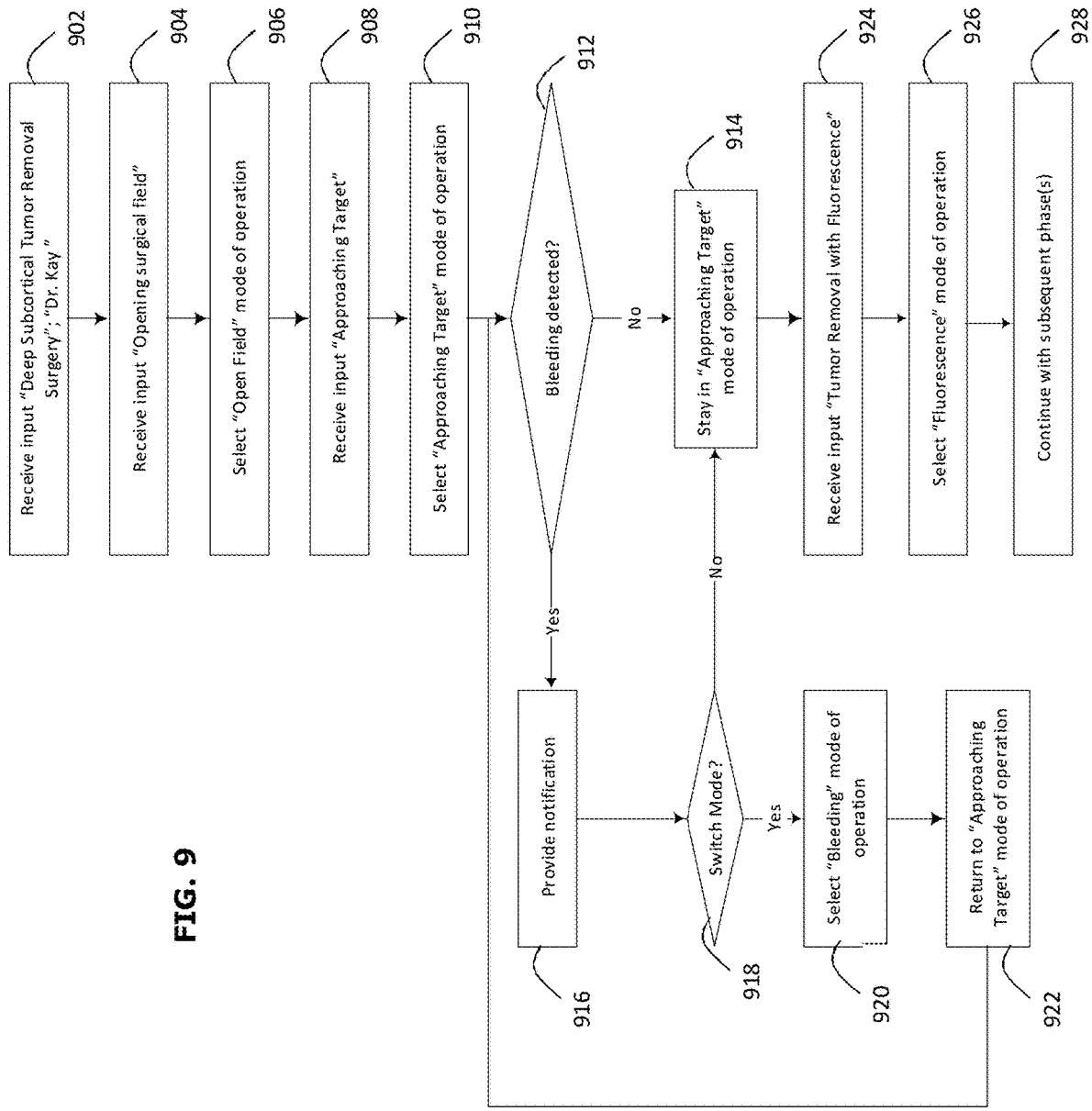
FIG. 9 is a flowchart illustrating an example of different modes of operation that may be used in a medical procedure.

FIG. 9 is a flowchart illustrating an example of how the surgical microscope system 500 may change to different modes of operation during a medical procedure. This example illustrates operation for an example tumor extraction procedure, and is not intended to be limiting.

At 902, input is received (e.g., via a user interface or voice input mechanism) indicating the type of medical procedure—deep subcortical tumor removal surgery—and the specific surgeon performing the procedure—Dr. Kay. This information may be used by the surgical microscope system 500 to determine the appropriate modes of operation relevant to a tumor removal surgery and/or determine any user-specific settings for Dr. Kay.

At 904, input is received indicating the first phase of the procedure—opening surgical field.

At 906, the system selects the appropriate mode of operation—the "open field" mode of operation. The "open field" mode may specify, for example, a large field of view, low brightness, long working distance, and no color enhancements. Autofocusing may be performed to keep the center of the captured image in focus. The surgeon may then perform the necessary steps (e.g., remove skin, skull and dura) for this phase of the procedure.

At 908, input is received indicating the next phase of the procedure—approaching target.

At 910 the system selects the appropriate mode of operation—the "approaching target" mode of operation. The "approaching target" mode may specify a field of view that matches the size of the surgical opening (e.g., determined using tracking information), medium brightness, long working distance and yellow enhancement. The surgeon may then navigate the surgical site (e.g., with assistance from the navigation system) until the target is reached.

At 912, as the surgeon navigates the surgical site, the surgical microscope system may continuously and automatically perform image analysis to detect any bleeding in the surgical site. If no bleeding is detected, the system remains in the "approaching target" mode of operation at 914.

If bleeding is detected, at 916 the system may provide a notification (e.g., visual and/or audio notification) indicating bleeding is detected. For example, the system may control a display to show the bleeding location (e.g., a picture-in-picture image focused on the bleeding site is shown). At 918, the notification may also offer the surgeon an option to confirm that the mode of operation should be switched to "bleeding" mode. If the surgeon chooses not to switch modes, then the system remains in the "approaching target" mode of operation at 914.

At 920, if the surgeon chooses to switch modes, the system selects the "bleeding" mode of operation. The "bleeding" mode of operation may perform autofocusing to keep the focus on the detected bleeding location, and may also reduce the red color setting.

At 922, when the surgeon has stopped the bleeding, the surgeon may provide input to indicate that bleeding has stopped and the system may return to the "approaching target" mode of operation. In some examples, the system may automatically detect that bleeding has stopped (e.g., using image analysis of the real-time captured image) and may return to the "approaching target" mode of operation (with or without the need for the surgeon to provide confirmation). The system then returns to 912 to continue monitoring the surgical site for possible bleeding, as the surgeon continues navigating the surgical site.

At 924, when the surgeon has reached the target, the system receives input indicating the next phase of the procedure—tumor removal with fluorescence.

At 926, the system selects the appropriate mode of operation—the "fluorescence" mode of operation. The "fluorescence" mode may specify a small field of view, UV illumination, medium working distance, fluorescence enhancement and autofocus on fluorescence in the captured image. The surgeon may then perform tumor removal (e.g., with the assistance of the navigation system).

At 928, subsequent phases of the medical procedure may be similarly carried out, with the surgical microscope system receiving input indicating each phase (e.g., exploring site, closing surgical field, etc.) and selecting the appropriate mode of operation (e.g., "exploration" mode, "closing" mode, etc.).

Although the present disclosure describes methods and processes with steps in a certain order, one or more steps of the methods and processes may be omitted or altered as appropriate. One or more steps may take place in an order other than that in which they are described, as appropriate. In many cases the order of process steps may be varied without changing the purpose, effect, or import of the methods described.

Although the present disclosure is described, at least in part, in terms of methods, a person of ordinary skill in the art will understand that the present disclosure is also directed to the various components for performing at least some of the aspects and features of the described methods, be it by way of hardware components, software or any combination of the two. Accordingly, the technical solution of the present disclosure may be embodied in the form of a software product. The software product includes instructions tangibly stored thereon that enable a processing device (e.g., a personal computer, a server, or a network device) to execute examples of the methods disclosed herein.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read only memory (ROM), volatile random access memory (RAM), non-volatile memory, cache or a remote storage device.

A computer-readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in any suitable programming language and may comprise software modules or engines, for example. Software instructions may be stored on storage media or on a computer readable medium that is readable by any suitable general or special purpose processing device, such as a processor. The processor may implement an operating system and may include any hardware and/or software that is necessary to implement the functionality of at least one of the embodiments described herein.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

All values and sub-ranges within disclosed ranges are also disclosed. Also, although the systems, devices and processes disclosed and shown herein may comprise a specific number of elements/components, the systems, devices and assemblies could be modified to include additional or fewer of such elements/components. For example, although any of the elements/components disclosed may be referenced as being singular, the embodiments disclosed herein could be modified to include a plurality of such elements/components. The subject matter described herein intends to cover and embrace all suitable changes in technology.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments. Selected features from one or more of the above-described embodiments may be combined to create alternative embodiments not explicitly described, features suitable for such combinations being understood within the scope of this disclosure.

The invention claimed is:

1. A surgical microscope system for use in a medical procedure, the surgical microscope system comprising:
    an optical assembly including a set of adjustable optics;
    one or more cameras coupled to the optical assembly for capturing at least one image of a field of view; and
    a controller coupled to the optical assembly for controlling the optical assembly to adjust the set of adjustable optics, the controller being coupled to the one or more cameras for receiving the captured image, the controller being configured to:
        set a first mode of operation to be a selected mode of operation, the first mode of operation corresponding to at least one phase of the medical procedure and defining at least one setting for adjusting the set of adjustable optics;
        while controlling the optical assembly to adjust the optics according to the at least one setting defined by the selected mode of operation:
            determine, from the captured image, an indication, presence of the indication signifying that a second mode of operation is applicable, the second mode of operation defining at least one other setting for adjusting the set of adjustable optics;
            change the selected mode of operation to be the second mode of operation; and
            control the optical assembly to adjust the optics according to the at least one other setting defined by the second mode of operation;
        the second mode of operation corresponding to an abnormal phase or emergency phase of the medical procedure, and the at least one other setting defined by the second mode of operation including at least one of a magnification setting or a focus setting to enhance viewing of a region associated with the abnormal phase or emergency phase.

2. The surgical microscope system of claim 1, wherein the first mode of operation is selected from a plurality of available modes of operation, each mode of operation corresponding to at least one respective phase of the medical procedure.

3. The surgical microscope system of claim 2, wherein at least one available mode of operation includes at least one setting that is defined based on historical usage of the surgical microscope system.

4. The surgical microscope system of claim 2, wherein at least one available mode of operation is a user-specific mode of operation including at least one setting that is defined based on user-specific preference or user-specific historical usage of the surgical microscope system.

5. The surgical microscope system of claim 1, wherein the controller is further configured to:

automatically analyze the captured image for an indicator, presence of the indicator signifying that the abnormal phase or emergency phase is applicable; and when the indicator is detected in the captured image, determine that the second mode of operation is applicable.

6. The surgical microscope system of claim 1, wherein the optical assembly comprises at least one of: a set of adjustable zoom optics or a set of adjustable focus optics.

7. The surgical microscope system of claim 1, wherein the surgical microscope is configured to be supported at a distal end of a robotic arm of a positioning system, and wherein the controller is further configured to:

generate control signals to control the positioning system or the robotic arm according to the selected mode of operation.

8. The surgical microscope system of claim 1, wherein the controller is further configured to:

prior to changing the selected mode of operation to the second mode of operation, generate a signal to cause a notification to be provided to indicate that the second mode of operation is applicable.

9. The surgical microscope system of claim 8, wherein the controller is further configured to:

change the selected mode of operation to the second mode of operation after receiving a signal indicating user confirmation of the second mode of operation.

10. The surgical microscope system of claim 1, further comprising a light source and a light sensor, wherein the controller is further configured to:

receive a signal from the light sensor representing a change in lighting conditions; and adjust at least one of the light source, the one or more cameras or a display coupled to the controller to adjust at least one of illumination, color settings, or brightness of the captured image according to at least one setting defined by the selected mode of operation.

11. The surgical microscope system of claim 1, wherein the selected mode of operation defines at least one setting based on location of a tracked tool, and wherein the controller is further configured to:

receive tracking information about the tracked tool; and control the optical assembly to adjust the optics according to the selected mode of operation, based on the tracking information.

12. A method for controlling a surgical microscope system during a medical procedure, the method comprising:

setting a first mode of operation to be a selected mode of operation, the first mode of operation corresponding to at least one phase of the medical procedure and defining at least one setting for adjusting a set of adjustable optics of the surgical microscope system, to enable the surgical microscope system to capture at least one image of a field of view;

while controlling the surgical microscope system according to the at least one setting defined by the selected mode of operation:

determining, from the captured image, an indication, presence of the indication signifying that a second mode of operation is applicable, the second mode of operation defining at least one other setting for adjusting the set of adjustable optics;

changing the selected mode of operation to be the second mode of operation; and controlling the surgical microscope system to adjust the optics according to the at least one other setting defined by the second mode of operation;

the second mode of operation corresponding to an abnormal phase or emergency phase of the medical procedure, and the at least one other setting defined by the second mode of operation including at least one of a magnification setting or a focus setting to enhance viewing of a region associated with the abnormal phase or emergency phase.

13. The method of claim 12, wherein the first mode of operation is selected from a plurality of available modes of operation, and at least one available mode of operation includes at least one setting that is defined based on historical usage of the surgical microscope system.

14. The method of claim 12, wherein the first mode of operation is selected from a plurality of available modes of operation, and at least one available mode of operation is a user-specific mode of operation including at least one setting that is defined based on user-specific preference or user-specific historical usage of the surgical microscope system.

15. The method of claim 12, further comprising:

automatically analyzing the captured image for an indicator, presence of the indicator signifying that the abnormal phase or emergency phase is applicable; and when the indicator is detected in the captured image, determining that the second mode of operation is applicable.

16. The method of claim 12, further comprising:

generating control signals to control a positioning system or a robotic arm supporting the surgical microscope system, according to the selected mode of operation.

17. A system for performing a medical procedure, the system comprising:

a surgical microscope including:

an optical assembly including a set of adjustable optics; and one or more cameras coupled to the optical assembly for capturing at least one image of a field of view;

a display for displaying the captured image; and a controller in communication with the surgical microscope, the controller being configured to:

set a first mode of operation of the surgical microscope to be a selected mode of operation, the first mode of operation corresponding to at least one phase of the medical procedure and defining at least one setting for adjusting the set of adjustable optics;

while controlling the optical assembly to adjust the optics according to the at least one setting defined by the selected mode of operation:

determine, from the captured image, an indication, presence of the indication signifying that a second mode of operation is applicable, the second mode of operation defining at least one other setting for adjusting the set of adjustable optics;

change the selected mode of operation to be the second mode of operation; and control the optical assembly to adjust the optics according to the at least one other setting defined by the second mode of operation;

the second mode of operation corresponding to an abnormal phase or emergency phase of the medical procedure, and the at least one other setting defined by the second mode of operation including at least one of a magnification setting or a focus setting to enhance viewing of a region associated with the abnormal phase or emergency phase.

18. The system of claim 17, further comprising:
a positioning system including a robotic arm, wherein the surgical microscope is supported at a distal end of the robotic arm;
wherein the controller is in communication with the positioning system and is further configured to:
  generate control signals to control the positioning system or the robotic arm according to the selected mode of operation.

19. The system of claim 17, further comprising:
a tracking system including a tracking camera for obtaining tracking information from a plurality of tracking markers;
wherein the selected mode of operation defines at least one setting based on location of a tool tracked by the tracking system; and
wherein the controller is in communication with the tracking system and is further configured to:
  control the surgical microscope system according to the selected mode of operation, based on the tracking information.

\* \* \* \* \*